United States Patent
Berg et al.

(10) Patent No.: US 8,739,798 B2
(45) Date of Patent: Jun. 3, 2014

(54) HEARING PROTECTION EARPLUG

(75) Inventors: Göran Berg, Tyringe (SE); Jörgen Hakannson, Tyringe (SE)

(73) Assignee: Uvex Arbeitsschutz GmbH, Fuerth (DE)

(*) Notice: Subject to any disclaimer, the term of this patent is extended or adjusted under 35 U.S.C. 154(b) by 76 days.

(21) Appl. No.: 12/676,969

(22) PCT Filed: Aug. 27, 2008

(86) PCT No.: PCT/EP2008/006991
§ 371 (c)(1),
(2), (4) Date: Jul. 12, 2010

(87) PCT Pub. No.: WO2009/033565
PCT Pub. Date: Mar. 19, 2009

(65) Prior Publication Data
US 2010/0307514 A1 Dec. 9, 2010

(30) Foreign Application Priority Data
Sep. 7, 2007 (DE) .......................... 10 2007 042 740

(51) Int. Cl.
*A61F 11/08* (2006.01)
(52) U.S. Cl.
USPC ............ 128/867; 128/864; 181/130; 181/135
(58) Field of Classification Search
CPC ..... A61F 11/06; A61F 11/08; A61F 2011/06; A61F 2011/08; A61F 2011/085
USPC ............ 128/864–868; 181/130, 135; 381/328
See application file for complete search history.

(56) References Cited

U.S. PATENT DOCUMENTS

| | | | |
|---|---|---|---|
| 1,016,877 A | 2/1912 | Elliott | |
| 1,830,198 A * | 11/1931 | French | 181/135 |

(Continued)

FOREIGN PATENT DOCUMENTS

| | | |
|---|---|---|
| DE | 7314145 U | 9/1973 |
| DE | 9302783 U1 | 4/1993 |

(Continued)

OTHER PUBLICATIONS

Japanese Office Action mailed Oct. 16, 2012, in corresponding Japanese application.

(Continued)

*Primary Examiner* — Patricia Bianco
*Assistant Examiner* — Kari Petrik
(74) *Attorney, Agent, or Firm* — Browdy and Neimark, PLLC

(57) ABSTRACT

In a hearing protection earplug made of foamed material, provision is made in order to attain a defined attenuation and avoid annoyances caused by self-generated sounds, that the surface of the hearing protection earplug has hollows in the area of the inner end face. The hearing protection earplug includes a main body having a central center longitudinal axis and in the direction of this central center longitudinal axis an axially inner end face and an axially outer end face. In the area of the inner end face, surface area enlarging inner hollows are provided, one of which, in the form of an inner central longitudinal hollow, extends inward longitudinally relative to the center longitudinal axis, starting from the inner end face. Also provided is an outer central longitudinal hollow that extends inward longitudinally relative to the center longitudinal axis, starting from the outer end face. The inner and the outer central longitudinal hollow are separated from each other by a continuous transverse wall extending perpendicular to the central center longitudinal axis.

6 Claims, 3 Drawing Sheets

(56) References Cited

U.S. PATENT DOCUMENTS

| | | | |
|---|---|---|---|
| 2,393,005 A * | 1/1946 | Veneklasen | 128/864 |
| 5,002,151 A * | 3/1991 | Oliveira et al. | 181/130 |
| 5,488,961 A | 2/1996 | Adams | |
| 6,148,821 A * | 11/2000 | Falco | 128/864 |
| 6,484,842 B1 | 11/2002 | Widmer et al. | |
| 6,820,717 B2 | 11/2004 | Fleming et al. | |
| 7,264,081 B2 * | 9/2007 | Bruck | 181/135 |
| 7,464,786 B2 | 12/2008 | Falco et al. | |
| 2003/0116165 A1 | 6/2003 | Huang | |
| 2003/0159878 A1* | 8/2003 | Hakansson et al. | 181/135 |
| 2004/0045558 A1* | 3/2004 | Taylor et al. | 128/864 |

FOREIGN PATENT DOCUMENTS

| | | | |
|---|---|---|---|
| DE | 69013927 T2 | 5/1995 | |
| DE | 20200638 U1 | 3/2002 | |
| DE | 202005009132 U1 | 8/2005 | |
| JP | S55-18825 Y | 2/1980 | |
| JP | 2003-512890 A | 4/2003 | |
| JP | 3124314 U | 7/2006 | |
| WO | 9825558 A1 | 6/1998 | |
| WO | 01/32113 A1 | 5/2001 | |
| WO | 0176520 A1 | 10/2001 | |
| WO | 2004064672 A2 | 8/2004 | |
| WO | 2005122981 A1 | 12/2005 | |

OTHER PUBLICATIONS

Japanese Notice of Reason of Refusal for Application 2013-026545 dated Nov. 19, 2013.

* cited by examiner

HEARING PROTECTION EARPLUG

FIELD

The invention relates to a hearing protection earplug consisting of a main body made of foamed material, wherein the main body has a central center longitudinal axis and in the direction of this central center longitudinal axis an axially inner end face and an axially outer end face.

BACKGROUND

Conventional hearing protection earplugs of this type are designed such that they close off the ear canal as completely as possible, in order to achieve maximum sound attenuation in this manner.

There are numerous fields of application, however, where even though it is necessary and desirable to attain a sound reduction, it is nonetheless important to maintain a means of communication through speech, or hear ambient noises or warning signals.

Another problem in conventional hearing protection earplugs consists in that they generate disturbing sounds, which are in particular otoacoustic emissions, bone conductions, or a transmission of one's own speech into the ear.

Such otoacoustic emissions are sounds that are generated within the ear itself and that accordingly practically emanate from within the ear. The emission occurs spontaneously or in response to an external acoustic stimulus. These sounds are generated by the hair cells of the organ of Corti in the cochlea and are emitted retrograde against the primary direction of the flow of sound, which is directed into the ear. This means that the emission leaves the organ of Corti via the oval window and accordingly also via the inner ear, in order to then pass through the middle ear via the auditory ossicles and enter via the eardrum into the outer ear canal, where they are then detectable by very sensitive measuring microphones.

Bone conduction refers to the conduction of sound vibrations through the bone substance surrounding the organ of hearing while bypassing the middle ear. Because of the high acoustic resistance of the cranial bone, the conscious perception of the bone conduction is usually masked by signals that are transmitted as airborne sound. When hearing protection is used, bone conduction leads to a distortion of sounds.

This so-called occlusion effect, which, besides bone conduction, is based also on tissue conduction, results in the user hearing his own voice not only distorted but also amplified, in the same way as other body sounds, such as e.g. breathing and blood flow, which has the effect that a certain block can be observed in the user, or isolation.

In DE 20 2005 009 132 U, WO 2005/122981 A1 and WO 2004/064672 A2, a hearing protection earplug is described in each case that has a hollow at one of its axial end faces. Another hearing protection earplug that is described in DE 202 00 638 U1 is designed substantially hollow and provided at one axial end face with a diaphragm. From DE 93 02 783 U1, DE 73 14 145 U1, DE 690 13 927 T2 and U.S. Pat. No. 6,484,842 B1, hearing protection earplugs are known, some of them comprising multiple parts, that have an axially continuous longitudinal hollow in each case, the opening widths of which can vary in the longitudinal direction. Additionally, hearing protection earplugs are disclosed in DE 690 13 927 T2, U.S. Pat. Nos. 1,016,877 and 6,484,842 B1 that are provided with hollows at their lateral circumferential surface.

SUMMARY

Proceeding from this, the invention has at its aim to improve a known hearing protection earplug of the type in question in such a way that the sound absorption or transmissivity can be adjusted in a defined manner and the generation of disturbing sounds is avoided or reduced.

This aim is achieved by a hearing protection earplug consisting of a main body made of foamed material, wherein the main body has a central center longitudinal axis and in the direction of this central center longitudinal axis an axially inner end face and an axially outer end face. In the inventive hearing protection earplug, surface area enlarging inner hollows are provided in the area of the inner end face, one of which, in the form of an inner central longitudinal hollow, extends inward longitudinally relative to the center longitudinal axis, starting from the inner end face. Additionally, an outer central longitudinal hollow is provided that extends inward longitudinally relative to the center longitudinal axis, starting from the outer end face. The inner and outer central longitudinal hollow are separated from each other by a transverse wall that extends perpendicular relative to the central center longitudinal axis.

The inner hollows form in particular cavities, whereby the surface area at the inner end of the hearing protection earplug is enlarged. This advantageous enlargement applies in particular to the surface that extends substantially transversely to the ear canal and upon which the endogenously generated sound waves impinge. Because of this surface area enlargement, as opposed to a spherical cap shaped surface in conventional hearing protection earplugs, the reflection of the sound waves is reduced and in particular a directional reflection is avoided.

When hearing protection earplugs were first being developed, they were produced from mineral wool, which, because of the structure of the mineral wool, also had certain hollows at the inner end face. In contrast to a hearing protection earplug made of foamed material according to the invention, however, these products that were known then had overall poor sound attenuation qualities.

The inner hollows or cavities may be in the form of a variety of different structures, such as e.g. golf-ball-like structures or structures in the style of an egg carton. It would also be conceivable to simply cut off the tip of an earplug after the (injection) molding process, such that the comparatively closed molded surface is partly removed and an open-pore structure of the foamed material, which otherwise exists only in the interior of the main body, exists on the inner end face. These open pores that then exist on the end face also are hollows according to the invention that effect the acoustically advantageous surface area enlargement.

Additionally, it proves advantageous to provide the central longitudinal hollow that extends into the interior, wherein, flush with same, a second central longitudinal hollow extends into the interior from the outer end face and the two central longitudinal hollows are separated from each other, however, by a transverse wall.

By means of these two central longitudinal hollows the effective material thickness of the hearing protection earplugs is reduced, as a result of which the transmissivity, e.g. for speech communication is increased in a defined manner. The hearing protection earplug according to the invention is accordingly partially sound transmitting. In particular, it is designed such that useful sound is able to pass through to a certain degree. The transverse wall that is provided in the interior acoustically uncouples the two central longitudinal hollows from each other. Loud exterior noises are absorbed in this manner and do not enter the inside of the ear. Additionally, undesired direct acoustic feedback of the sound pressure levels that are present in the inner and outer central longitudinal hollow is prevented. Furthermore, the transverse wall also offers an advantage from a production engineering aspect. It ensures that during injection molding of the hearing protection earplugs the ejection can take place by means of compressed air. Despite the material weakening that is provided according to the invention, the hearing protection earplug is still sufficiently sturdy as a whole, such that it can be inserted into the ear canal in a defined manner and without difficulty. Moreover, the inner central longitudinal hollow, as already explained above, also has an advantageous effect in weakening the reflection of sounds back into the inside of the ear.

In particular, provision can be made that the surface area enlarging inner hollows at least partly or in some areas also incorporate circumferential-surface hollows. These circumferential-surface hollows are provided on a circumferential surface of the main body and extend in the direction of the central center longitudinal axis. They are furthermore preferably designed channel-like and extend starting from a lateral area of the circumferential surface in particular to within the vicinity of an opening of the inner central longitudinal hollow disposed at the inner end face. With their partial areas that extend to or into the inner end face, they likewise contribute to reducing the potentially inwardly directed sound wave reflections that occur in conventional hearing protection earplugs at the inner face.

This embodiment furthermore achieves that the hearing protection earplug has a good fit without exerting pressure onto the inside of the ear canal. The good fit is achieved also as a result of the plug not having to be shortened for the purpose of reducing the attenuation behavior and adjusting a defined attenuation.

Advantageously, for example, four such circumferential-surface hollows can be provided that are evenly spaced about the circumferential surface. This creates a kind of star-shaped configuration in the top view.

In a further embodiment of the invention, provision can be made that the frontal outer end of the hearing protection earplug has a collar-like widening. The outer end face can be provided with at least one base hollow, into the base bottom of which the outer central longitudinal hollow opens. This makes the hearing protection earplug easier to compress prior to inserting it into the ear. This facilitates its use.

The invention will be explained in greater detail below based on a preferred illustrative embodiment in conjunction with the drawing.

DETAILED DESCRIPTION

Figure 1:
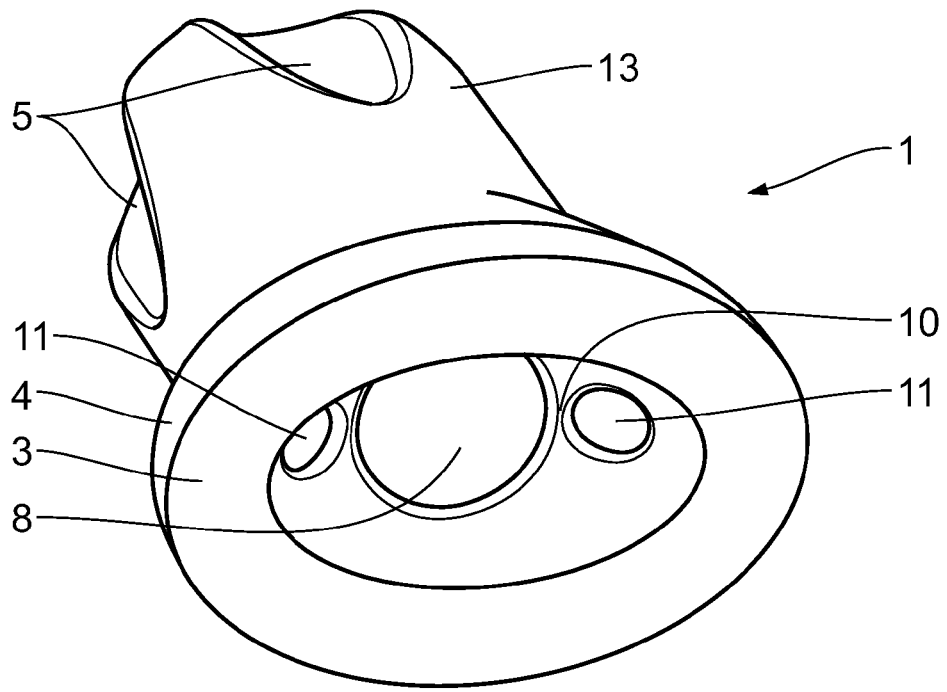
FIG. 1 shows an illustrative embodiment of a hearing protection earplug in a perspective illustration from an oblique view onto the outer end face relative to the position of use.
Figure 2:
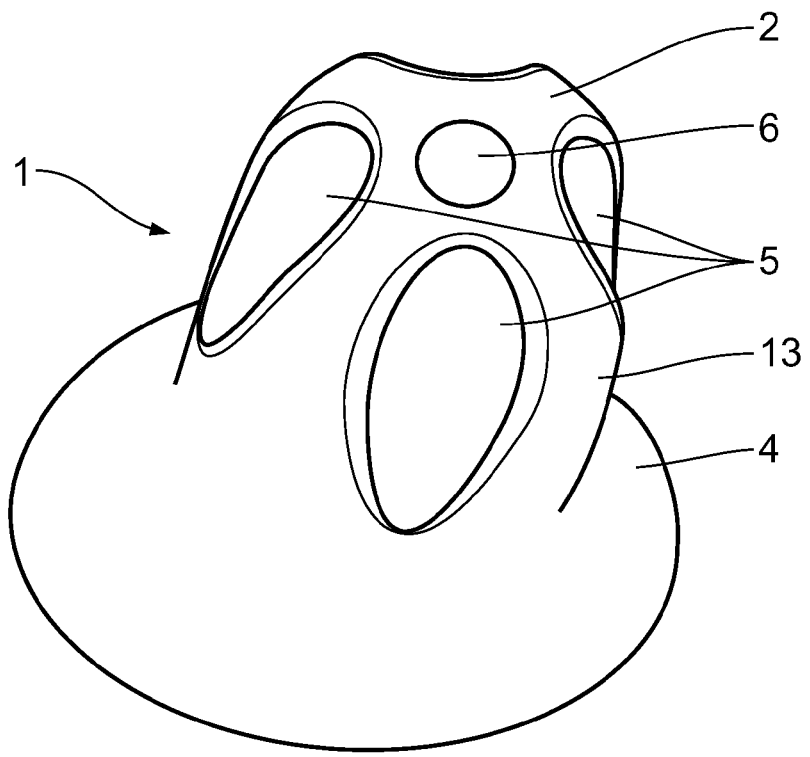
FIG. 2 shows the hearing protection earplug according to FIG. 1 in a perspective illustration from an oblique view onto the inner end face relative to the position of use.
Figure 3:
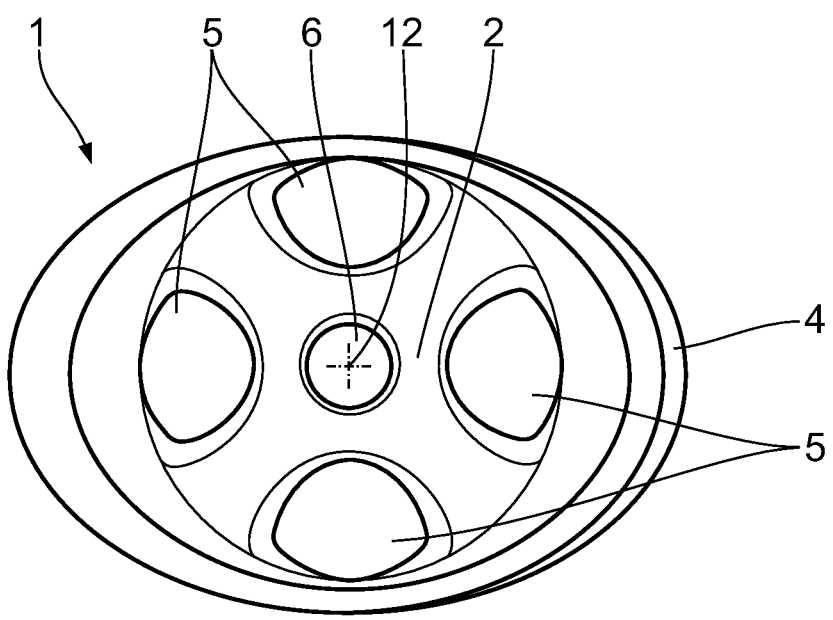
FIG. 3 shows the hearing protection earplug according to FIGS. 1 and 2 in a top view onto the inner end face relative to the position of use.
Figure 4:
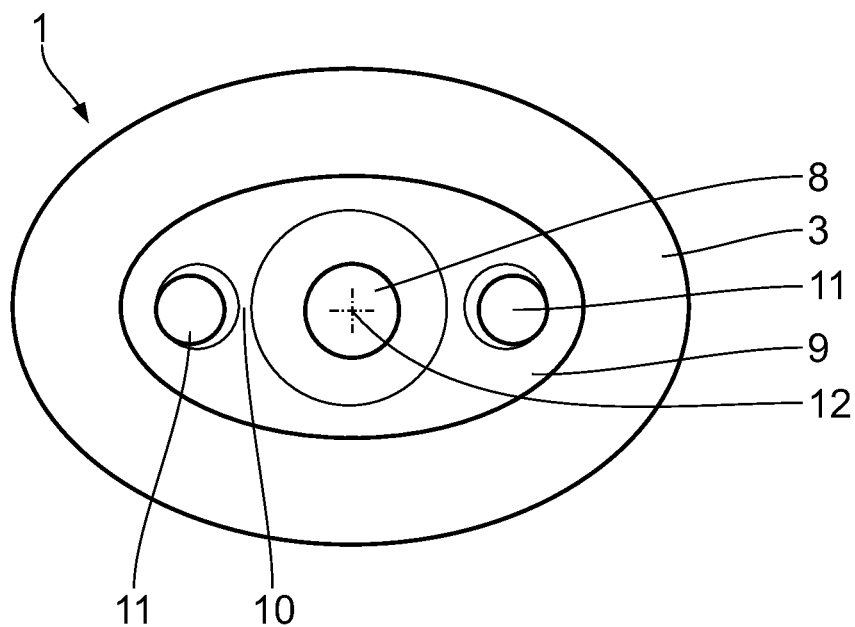
FIG. 4 shows the hearing protection earplug according to FIGS. 1 to 3 in a top view onto the outer end face relative to the position of use.
Figure 5:
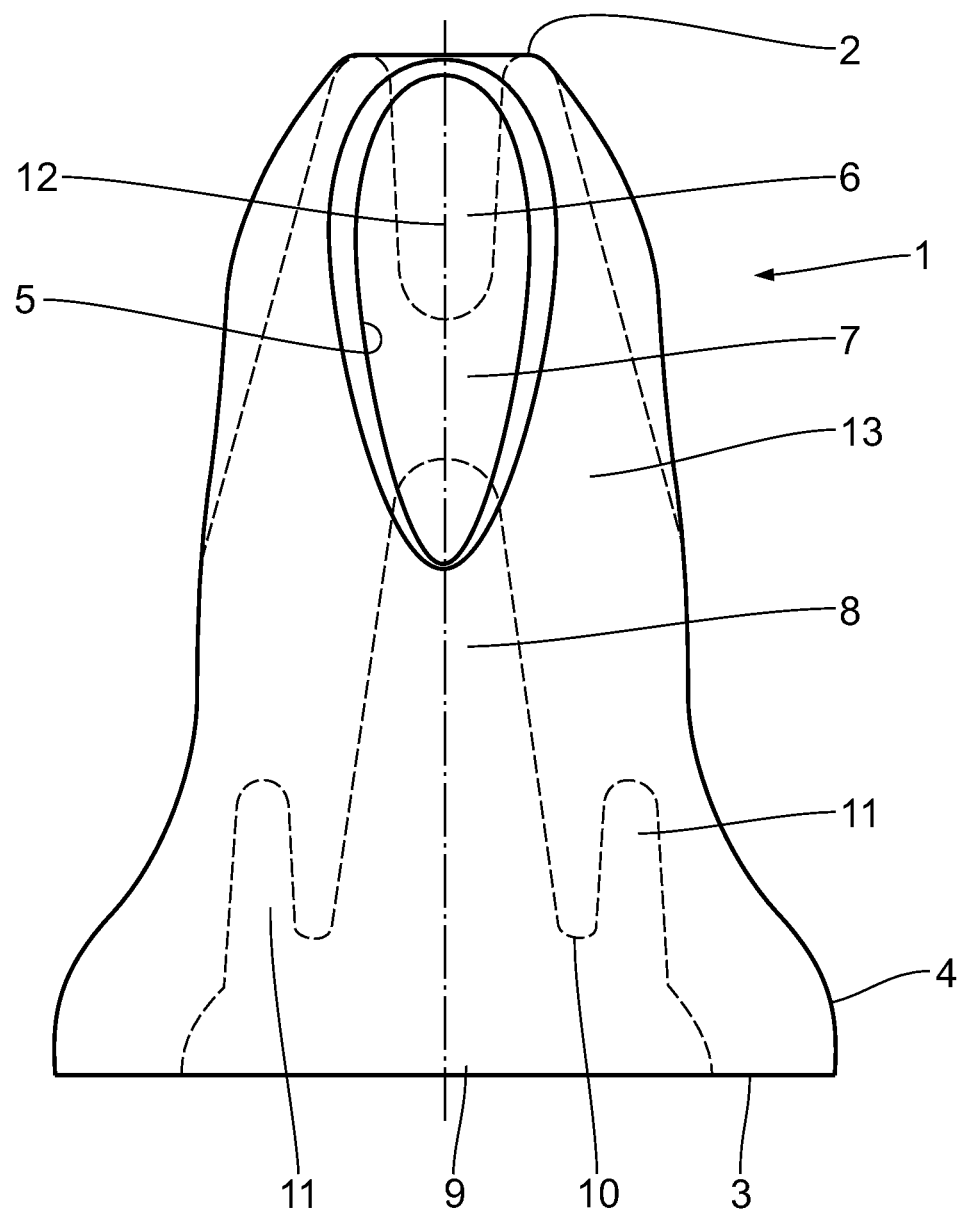
FIG. 5 shows the hearing protection earplug according to FIGS. 1 to 4 in a side view.

An illustrative embodiment shown in FIGS. 1 through 5 of an inventive one-piece hearing protection earplug is made of foamed material and has an approximately bell-shaped main body 1. It has an inner end face 2 which, in the position of use, is inserted toward the inside of the ear canal into the ear, and an outer end face 3 which, in the position of use, faces toward the outside. The main body 1 ends, via a collar-like widening 4, in the outer end face 3.

The main body 1 has a central center longitudinal axis 12—the axial direction of which substantially also corresponds to the direction of insertion of the hearing protection earplug—and a circumferential surface 13. It is provided on its circumferential surface 13 with channel-like circumferential-surface hollows 5 extending in the longitudinal direction, i.e. in the direction of the central center longitudinal axis 12, that extend to within the inner end face 2 and that result in a texturing of same and in particular in a formation of cavities, as can be seen particularly well in FIG. 3. The circumferential-surface hollows 5 are approximately oval in the top view (see FIGS. 2 and 5).

From the center of the inner end face 2, a cylindrical or slightly conical central longitudinal hollow 6 extends inward longitudinally relative to the center longitudinal axis 12 into the main body 1. It reaches to a transverse wall 7, from the side of which facing away from the inner central longitudinal hollow 6 a likewise cylindrical or slightly conical outer central longitudinal hollow 8 extends outward to a widened pot-shaped base hollow 9 that occupies the center of the outer end face 3. If a conical shape is provided for the inner and/or outer central longitudinal hollow 6 or 8, same is designed such that the opening width thereof increases toward the end face 2 and/or 3 and decreases toward the transverse wall 7. The outer central longitudinal hollow 8 likewise extends longitudinally relative to the center longitudinal axis 12. The continuous transverse wall 7 extends perpendicularly to the center longitudinal axis 12. It does not have any longitudinal opening or connecting channel in the direction of the center longitudinal axis 12, such that it completely separates the inner and outer central longitudinal hollow 6 and 8 from each other. The transverse wall 7 therefore is also a partition wall in this respect.

In the inventive hearing protection earplug, provision is made in order to attain a defined attenuation and avoid annoyances caused by self-generated sounds, that the surface of the hearing protection earplug is provided in the area of the inner end face 2 with the surface area enlarging hollows, namely with the inner central longitudinal hollow 6 and at least in some areas thereof with the circumferential-surface hollows 5.

Disposed laterally next to the outer central longitudinal hollow 8 are two additional cylindrical fastening hollows 11. They extend inward starting from a base bottom 10 of the base hollow 9 parallel to the central longitudinal hollow 8 and parallel to the center longitudinal axis 12 into the main body 1. They serve to accommodate a fastening end section of a connecting cord, with which two hearing protection earplugs can be connected to each other. A user can then place the connecting cord with the affixed hearing protection earplugs around his neck, such that the hearing protection earplugs are always handy.

The invention claimed is:

1. A hearing protection earplug comprising a main body (1) consisting of foamed material, wherein
    a) the main body (1) has a central center longitudinal axis (12) and in the direction of said central center longitudinal axis (12) an axially inner end face (2) and an axially outer end face (3),
    b) surface area enlarging inner hollows (5, 6) are provided in the area of the inner end face (2), and include an inner central longitudinal hollow (6), which extends inward longitudinally relative to the center longitudinal axis (12), starting from the inner end face (2), c) an outer central longitudinal hollow (8) is provided that extends inward longitudinally relative to the center longitudinal axis (12), starting from the outer end face (3), d) the inner and the outer central longitudinal hollows (6, 8) are separated from each other by a continuous transverse wall (7) extending perpendicular relative to the central center longitudinal axis (12), and e) the surface area enlarging inner hollows (5, 6) further include at least partly circumferential-surface hollows (5) disposed at a circumferential outer surface (13) of the main body (1) and extending in the direction of the central center longitudinal axis (12) and extending to within the inner end face (2) resulting in a texturing of the inner end face (2) and in a formation of cavities in the inner end face (2), and wherein the hearing protection earplug is formed from an injection molded material and in one piece.

2. A hearing protection earplug according to claim 1 wherein four of the circumferential-surface hollows (5) are provided and are evenly distributed about the circumferential surface (13).

3. A hearing protection earplug according to claim 1, wherein the circumferential-surface hollows (5) are channel-shaped and extend starting from a lateral area of the circumferential surface (13) to within the vicinity of an opening of the inner central longitudinal hollow (6) disposed at the inner end face (2).

4. A hearing protection earplug according to claim 1, wherein, in the area of the outer end face (3), a collar-like widening (4) is provided.

5. A hearing protection earplug according to claim 1, wherein, at the outer end face (3) a base hollow (9) is provided, into the base bottom (10) of which the outer central longitudinal hollow (8) opens.

6. A hearing protection earplug according to claim 1, wherein, laterally next to the outer central longitudinal hollow (8) at least one additional longitudinal hollow (11) is provided that extends parallel to the outer central longitudinal hollow (8) and the central center longitudinal axis (12) into the main body (1).

* * * * *